United States Patent
Menetrier

(10) Patent No.: US 11,191,716 B1
(45) Date of Patent: Dec. 7, 2021

(54) PROCESS FOR PREPARING POTENT PLANT BASED COSMETIC ACTIVES AND APPLICATION TO AN ANTIPERSPIRANT ACTIVE

(71) Applicant: PHISAO, Saint-Saturnin-de-Lucian (FR)

(72) Inventor: David Menetrier, Damparis (FR)

(73) Assignee: PHISAO, St Saturnin de Lucian (FR)

( * ) Notice: Subject to any disclaimer, the term of this patent is extended or adjusted under 35 U.S.C. 154(b) by 0 days.

(21) Appl. No.: 16/577,395

(22) Filed: Sep. 20, 2019

Related U.S. Application Data

(60) Provisional application No. 62/733,659, filed on Sep. 20, 2018.

(51) Int. Cl.
*A61K 8/97* (2017.01)
*A61K 8/92* (2006.01)
*A61Q 15/00* (2006.01)

(52) U.S. Cl.
CPC .............. *A61K 8/97* (2013.01); *A61K 8/922* (2013.01); *A61Q 15/00* (2013.01)

(58) Field of Classification Search
CPC ........... A61K 8/97; A61K 8/922; A61Q 15/00
See application file for complete search history.

(56) References Cited

U.S. PATENT DOCUMENTS

| | | | | |
|---|---|---|---|---|
| 6,534,046 B1 * | 3/2003 | Golz-Berner | ........ | A61K 8/9794 424/65 |
| 2006/0018855 A1 * | 1/2006 | Batista | .................. | A61Q 15/00 424/65 |
| 2009/0117146 A1 * | 5/2009 | Khan | .................... | A61K 36/81 424/195.17 |
| 2011/0311661 A1 * | 12/2011 | Behr | .................... | A61K 8/9789 424/750 |

OTHER PUBLICATIONS

Ngoualem et al. Chemistry and Functionalities of Lake Deposits and Plant-Based Salts Used in Food Preparations: A Review. Food Chem. Aug. 15, 2020; 321:126674 (10 pages). (Year: 2020).*
Ngoualem et al. Variability and Functionalities of Salts Used in Traditional African Food Preparations. Journal of Scientific Research & Reports 2019, 24(3): 1-14. (Year: 2019).*

* cited by examiner

*Primary Examiner* — Robert A Wax
*Assistant Examiner* — Olga V. Tcherkasskaya
(74) *Attorney, Agent, or Firm* — Maier & Maier, PLLC

(57) ABSTRACT

A process for preparing a potent plant based active, the process includes creating a plant salt, a plant tincture, and a plant essential oil and adding the salt either alone or with the essential oil and/or tincture to a cosmetic product as an active ingredient.

10 Claims, 2 Drawing Sheets

PROCESS FOR PREPARING POTENT PLANT BASED COSMETIC ACTIVES AND APPLICATION TO AN ANTIPERSPIRANT ACTIVE

BACKGROUND

1. Field of the Invention

The present invention relates generally to cosmetic preparation systems, and more specifically, to a process for developing a potent, plant based active for use in various cosmetics. The process of the present invention will be further elaborated on in relation to antiperspirants.

2. Description of Related Art

Alchemy is currently referred to as the mother of modern chemistry, with roots reaching back to Ancient Egypt. The principle is to separate, purify, and recombine matter. Each matter contains three principles: sulfur, mercury, and salt. Those have nothing to do with the commonly known chemical elements with the same names. The application of alchemical principles in the plant kingdom is called spagyrics. This process utilizes various procedures to separate components of a plant and therefore make the components more potent, which may have health benefits, such as providing a cure for various ailments.

The conventional process of spagyrics has always had the purpose of enhancing the potency of the plant extracts for therapeutic effects, such as to find cures and a means to counter body disorders.

Accordingly, it is an object of the present invention to apply the principles above to the cosmetic industry, wherein the potency of the plants can be utilized in cosmetics to provide benefits when applied to the skin as opposed to being ingested. The present invention utilizes spagyrics to obtain new cosmetic actives, being more potent, and thus able to compete with the standards of the cosmetic actives industry.

Cosmetic preparation systems are well known in the art and are effective means for users to take care of their skin. One conventional cosmetic is antiperspirants. A product is considered as an antiperspirant by the FDA if the product causes at least a 20% reduction in sweat in 50% of the test population. Conventional antiperspirants typically utilize aluminum salts which have been shown to be effective at reducing perspiration. However, the use of aluminum salts has caused potential health concerns, which has led to the development of alternative products, however, most of these alternative products are less effective at reducing perspiration.

Accordingly, it is an object of the present invention to provide for an antiperspirant that is created with novel ingredients that is both beneficial to the user from a health perspective and also effective at reducing perspiration.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
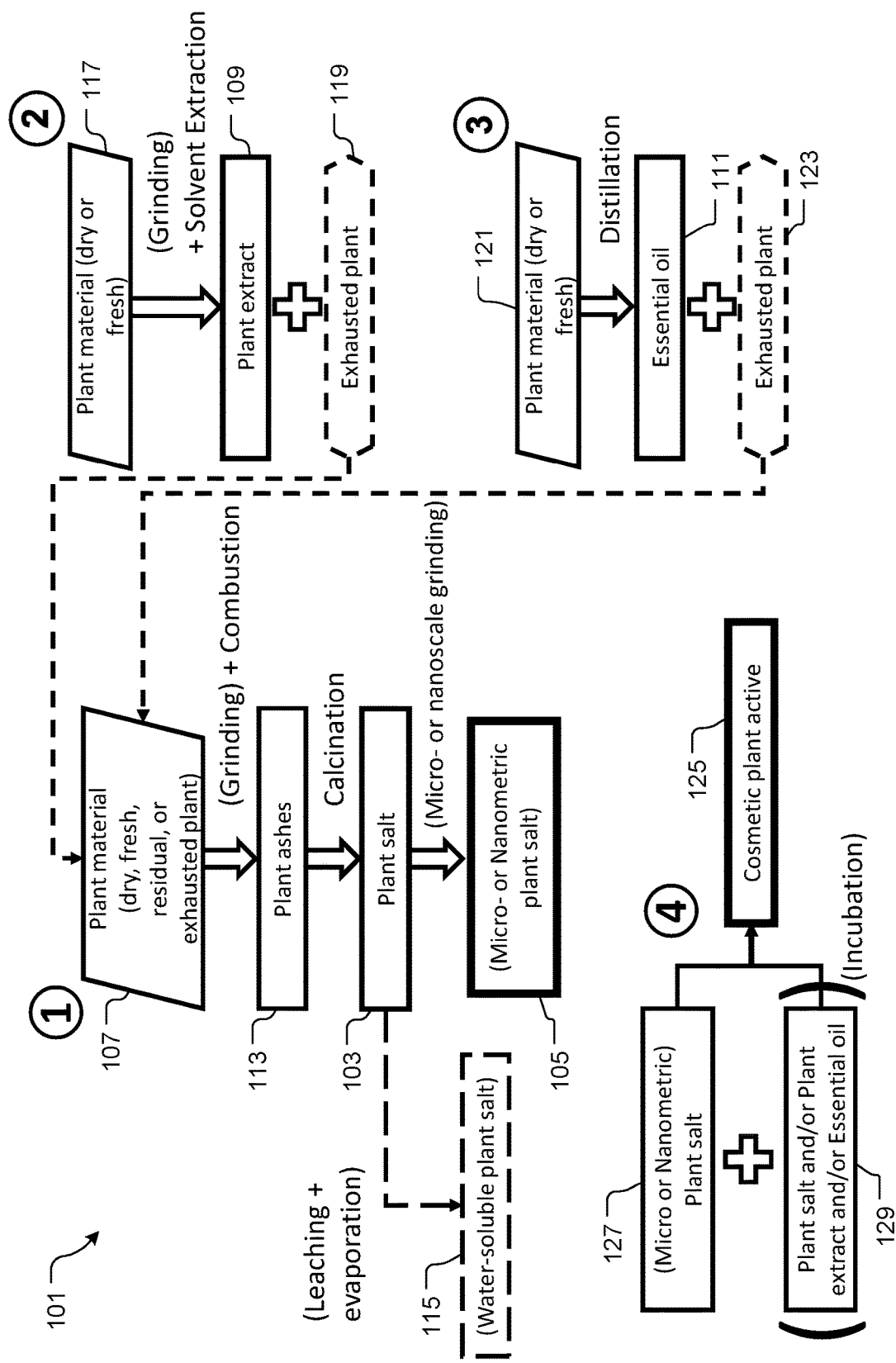
FIG. 1 is a flowchart of the process used to obtain potent plant based cosmetic actives in accordance with a preferred embodiment of the present invention.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional cosmetic systems. Specifically, one object of the invention is to provide plant-based cosmetic actives that are much more potent than those obtained by the means conventionally used. This is achieved through the synergy of two to three critical parts of plants: their salts, their tincture, and their essential oil. The use of plant salts in association with tinctures and/or essential oils coming from one to several plants, allows the creation of natural cosmetic actives outperforming those stemming from conventional processes known to the person skilled in the art. The present invention further relates to the process of increasing the performances of conventional extracts, through the use of plant salts. Although the process is suitable for use with various applications, the process will specifically be explained in relation to antiperspirants, wherein the process results in an efficient solution as an alternative to aluminum salts, relying on sage and horsetail salts. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a flowchart 101 of a process for creating potent plant based actives for cosmetics in accordance with a preferred embodiment of the present application. It will be appreciated that the process overcomes one or more of the above-listed problems commonly associated with conventional cosmetic systems.

In the contemplated embodiment, process 101 first includes the creation of a plant salt 103. This plant salt 103 is then preferably ground to a micro or nanometric plant salt 105. To create the plant salt 103, the first step is to select a first plant material 107 from a first plant. It should be appreciated that the first plant material 107 may be dry, fresh, residual, or an exhausted plant (which may come from the creation of an extract/tincture 109 or essential oil 111, as will be discussed.

Next, the plant material is ground into small pieces and then burnt to create plant ashes 113. Then finally, in order to create the salt 103, a process called calcination is used, as is known in the art. This process includes the ashes being calcined progressively, from 100° C. to 400-900° C., during at least 5 hours, the precise length of time depending on the chosen plant material. In some embodiments, the salt 103 is further processed through leaching the ashes with water to create a solution, filtering the solution, and evaporating the water from the solution to create water soluble plant salts 115. The resulting powder created from the calcination process and the leaching/evaporation process is crushed into fine particles, preferably to a micrometric or nanometric size.

The second part of the process is to create the plant extract/tincture 109. For this process, a second plant material 117 is selected. It should be appreciated that the plant material used for the extract/tincture 109 and the salt 103 can be the same plant, same type of plant, or different plants. In order to create the extract 109, the plant material goes through a grinding process, wherein the second plant matter is ground into smaller pieces, and then the user will perform solvent extraction through a fluid extraction process to create the extract/tincture 109. The solvent extraction process may utilize aqueous, and/or organic solvents as those skilled in the art will know. As organic solvents, can be quoted for instance C1-C4 alcohols like ethanol and isopropanol, polyols like propyleneglycol, glycerol, monoethylether, diethylether, acetone, ethyl acetate, hexane, benzylic alcohol, and their combination. Ethanol is usually preferred.

Using supercritical fluids is also a way of preparing the plant extract/tincture, using solvents such as carbon dioxide, water, methane, ethane, propane, ethylene, propylene, methanol, ethanol, acetone, and their combination.

This process may result in exhausted plant matter 119 which can then be utilized during the salt creation.

The third step is to create the essential oil 111. For this process, another plant material 121 is selected, which may be dry or fresh. Again, it should be appreciated that the plant material used to create the essential oil and the plant material that is used to create the salt can come from the same plant or different plants. The plant material 121 is processed through a distillation process to then create the essential oil 111, again potentially resulting in exhausted plant matter 123 that can be used in the salt making process. The distillation process may be completed with steam, preferably at a low pressure (less than 1 atm), and the essential oil is obtained through decantation from the distilled water.

Lastly, as shown, the final stage is to create the cosmetic plant active 125 which can be used in a cosmetic preparation, thereby imparting the benefits of the active to the cosmetic preparation. For creation of the active 125, the plant salt 127 may be utilized alone, or in combination with the extract and/or essential oil 129. If the later, the combination of the salt and extract and/or essential oil will likely need to be incubated for a predetermined time period. The chosen salt(s), tincture(s), and/or essential oil(s), are unified, then sealed, and left in an incubator for 3 to 40 days, preferably 3 to 7 days, at 30-100° C., preferably at 30-65° C., preferably at 37-40° C. The plant-based active is then ready to be used.

It should be appreciated that one of the unique features believed characteristic of the present application is the creation of the plant active via a combination of plant salt, plant tincture, and plant essential oil. The plants for salt, tincture, and/or essential oil are thoroughly chosen according to the desired application (antiperspirant, deodorant, astringent, soothing, anti-redness, anti-aging, anti-inflammatory, healing, tonifying, photoprotective, etc.), and according to the known properties of each extract of the plants.

Figure 2:
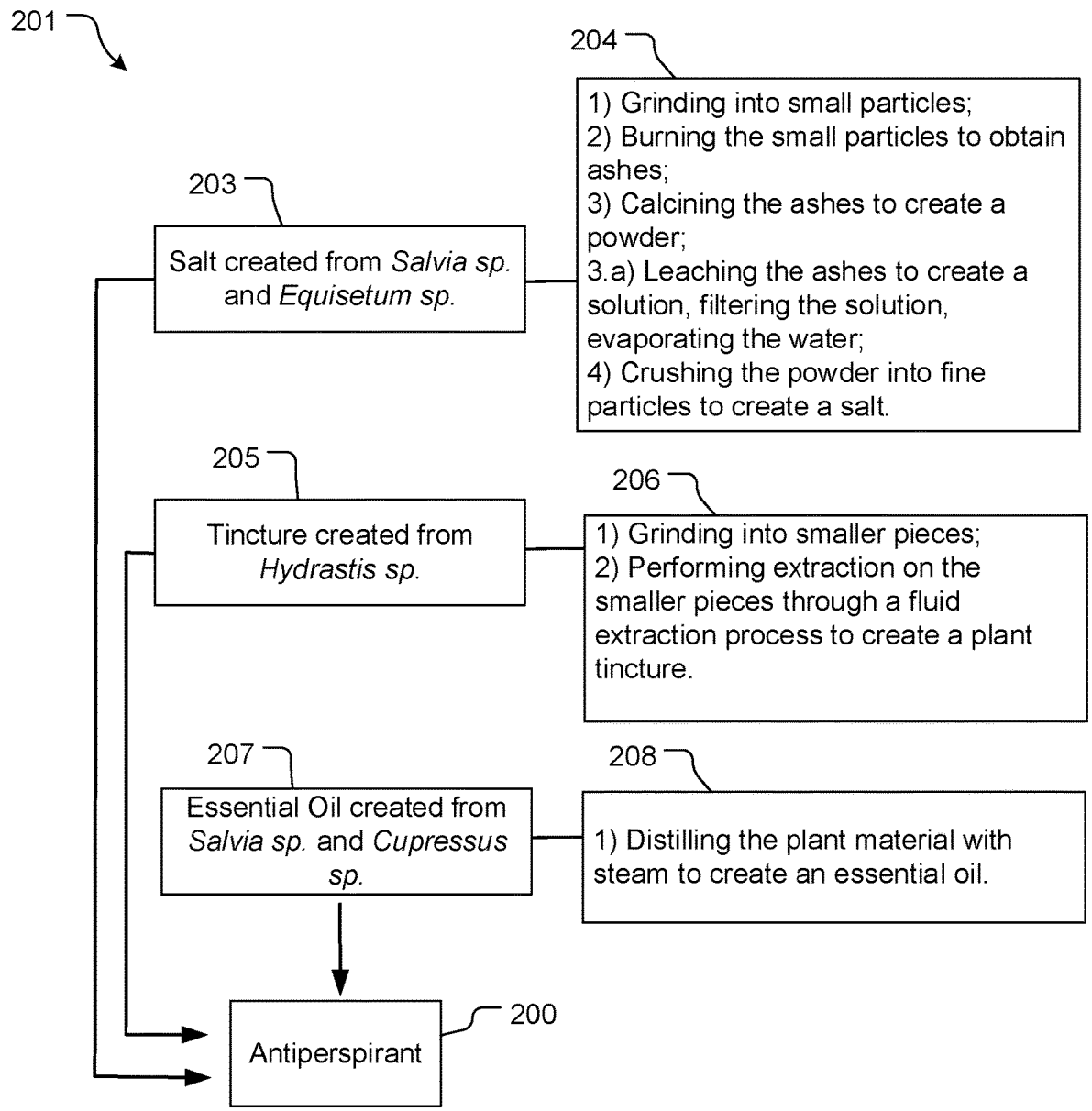
FIG. 2 is a flowchart of the process of creating an antiperspirant utilizing the process of FIG. 1 in accordance with the present invention.

In FIG. 2, a flowchart 201 depicts the method of use of the process above to create specifically an antiperspirant 200. In the preferred embodiment, the salt is created from specific plants, namely *Salvia* sp. (for example *Salvia officinalis*) and *Equisetum* sp. (for example *Equisetum arvense*), as shown with box 203. This process is accomplished as previously discussed, as shown with box 204. Then, the plant extract/tincture is created from *Hydrastis* sp. (for instance *Hydrastis canadensis*), as shown with box 205. Again, this process is accomplished as previously discussed and shown with box 206. Finally, the essential oil is created from *Salvia* sp. (for instance *Salvia officinalis*, and *Salvia sclarea*) and *Cupressus* sp. (for instance *Cupressus sempervirens*), as shown with box 207. The creation of the essential oil being completed as previously discussed and shown with box 208.

Sage and horsetail species have been identified through bibliography as potent candidates for antiperspirant properties. However, it has been seen that the existing extracts available on the market don't reach the performances of the most recent aluminum salts, namely a 25% of reduction of perspiration after 24 h for some alternatives, while the most performing aluminium salts reach 60% of reduction of perspiration after 24 h.

The following are a plurality of examples, however, these are not to be considered limiting to the present invention:

EXAMPLE 1:50 g of flowered heads of *Hypericum perforatum* were placed in a Soxhlet apparatus, and 800 mL of 96° ethanol were heated in the flask below. After 7 cycles of extraction, another 50 g batch replaced the exhausted one. This procedure was repeated 3 times. The resulting tincture of *Hypericum perforatum* has a deep dark red colour. The four batches of exhausted *Hypericum perforatum* are burnt, and then put in an oven from room temperature to 600° C., during 15 h. The resulting salt is white greyish, and is crushed into a fine powder. Salt of *Hypericum perforatum*, tincture of *Hypericum perforatum*, and essential oil of

*Matricaria recutita* are put together in a proportion of 2:1:1, and then installed in an incubator for 21 days at 40° C. The resulting active has strong healing and anti-inflammatory properties.

EXAMPLE 2: 71 g of flowers of *Papaver rhoeas* were placed in a Soxhlet apparatus after being finely ground, and 600 mL of 96° ethanol were heated in the flask below. After 17 h of extraction time, the plant is still delivering some colour, but the extraction is stopped. The resulting tincture of *Papaver rhoeas* has a deep ruby colour. The exhausted *Papaver rhoeas* is burnt with a gas burner 30 min, obtaining 7.80 g of *Papaver rhoeas* ashes, and then put in an oven from room temperature to 900° C., during 21 h. The resulting 4.5 g of *Papaver rhoeas* salt is blue. On the same model, the salt of *Calendula officinalis* can be obtained through calcining the residual plants from a conventional extraction process. Thus, combining salt of *Calendula officinalis*, salt of *Papaver rhoeas*, tincture of *Papaver rhoeas*, and essential oil of *Citrus aurantium* ssp. *amara* in proportions 10:1:7:5, allows the creation of a deeply soothing skin active. This active is finally placed for 7 days in an incubator at 37° C.

EXAMPLE 3: A 50% hydroalcoholic extract of saffron threads (*Crocus sativus*) was obtained by macerating 25 g of ground saffron threads in 300 mL of a 50% hydroalcoholic solution during 4 h at room temperature with constant stirring. The macerate was then double filtered, and the residue was burnt, and then calcined for 10 hours at 500° C. The resulting salt of saffron threads is orange. This salt is ground to a nanometric scale. Adding this salt to the conventional extract obtained through maceration, boosts the revitalizing effects of saffron.

EXAMPLE 4: 300 g of horsetail (*Equisetum arvense*) sterile aerial parts are burnt, to obtain 54.47 g of horsetail ashes. 300 g of sage (*Salvia officinalis*) leaves are burnt, to obtain 32.88 g of sage leaves ashes. 32.76 g of sage ashes (80%), and 8.19 g of horsetail ashes (20%) are mixed together, and calcined from 100° C. to 600° C. during 11 hours: 26.81 g of sage and horsetail salts (called Active Alpha) are obtained. The following maceration is prepared, called Active Beta: 5 parts of Active Alpha; 1 part of essential oil of clary sage (*Salvia sclarea*); 1 part of essential oil of common sage (*Salvia officinalis*); 1 part of essential oil of Mediterranean cypress (*Cupressus sempervirens*); 2 parts of goldenseal (*Hydrastis canadensis*) root ethanolic extract at a 1:5 plant:solvent ratio. The mixture is sealed in a container, and left 5 days at 50° C. in an incubator. A cosmetic formula is then being made: 2 parts of Active Beta (2%); 2 parts of NaCl; 5 parts of tween 20; 91 parts of water; The mixture is applied under one axilla, and gives a 30 to 50% perspiration reduction (FDA protocol, hot room at 40° C.) after 24 h.

EXAMPLE 5: 500 g of horsetail (*Equisetum arvense*) sterile aerial parts are burnt, to obtain 84.2 g of horsetail ashes. These ashes are calcined from 100° C. to 700° C. during 7 hours: 53.98 g of horsetail salts are obtained. 500 g of sage (*Salvia officinalis*) leaves are burnt, to obtain 50.55 g of sage leaves ashes. These ashes are calcined from 100° C. to 700° C. during 7 hours: 26.14 g of sage salts are obtained. The horsetail salts are mixed with essential oil of *Cupressus sempervirens* on a 1:1 ratio, sealed in a container, and put into the incubator during 21 days at 40° C. This gives Active Gamma. The sage salts are mixed with essential oil of *Salvia sclarea* on a 1:1 ratio, sealed in a container, and put into an incubator during 21 days at 40° C. This gives Active Delta. A cosmetic formula is then being prepared: 25 parts of Active Gamma (0.5%); 25 parts of Active Delta (0.5%); 450 parts of K2CO3 salt; 4645 parts of water. After 3 applications (once/day during 3 days), a decrease of 61% of perspiration is obtained (FDA protocol, hot room at 40° C.) after 24 h. This reaches the levels of the most performing aluminum salts.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A process for preparing a potent plant based active, the process comprising:
   selecting a first plant material from a first plant, the first plant material being chosen from aerial parts of the first plant;
   burning the first plant material to create plant ashes of the first plant material;
   applying a heat treatment to the plant ashes at a temperature from 200° C. to 900° C. during at least 5 hours and up to 5 days to create a powder; and
   crushing the powder into micrometric or nanometric particles to create the potent plant based active;
   wherein the potent plant based active is utilized in a cosmetic preparation.

2. The process of claim 1, further comprising:
   leaching the powder with water to create a solution;
   filtering the solution to remove any undissolved particles; and
   evaporating the water from the solution to obtain water-soluble particles of the powder.

3. The process of claim 1, further comprising:
   selecting a second plant material from a second plant, the second plant material being chosen from aerial parts of the second plant;
   grinding the second plant material into pieces;
   performing extraction on the second plant material through a fluid extraction process to create a plant extract;
   combining the particles of the first plant material and the plant extract into the cosmetic preparation; and
   incubating the cosmetic preparation at a temperature of 30-100° C. for a time period between 1 hour and 6 weeks.

4. The process of claim 3, wherein the first plant and the second plant are the same.

5. The process of claim 1, further comprising:
   selecting a third plant material from a third plant, the third plant material being chosen from aerial parts of the third plant;
   distilling the third plant material with steam to create an essential oil from the third plant material;
   combining the potent plant based active and the essential oil to create a cosmetic preparation; and
   incubating the cosmetic preparation at a temperature of 30-100° C. for a time period between 1 hour and 6 weeks.

6. The process of claim 5, wherein the first plant and the third plant are the same.

7. A process for preparing an antiperspirant, the process comprising:

selecting a first plant material from either *Salvia* sp. or *Equisetum* sp., the first plant material being chosen from aerial parts of *Salvia* sp. or *Equisetum* sp.;

burning the first plant material to create plant ashes from the first plant material;

applying a heat treatment to the plant ashes at a temperature from 200° C. to 900° C. during at least 5 hours and up to 5 days to create a powder; and crushing the powder into micrometric or nanometric particles to create a potent plant based active from *Salvia* sp. or *Equisetum* sp.;

wherein the potent plant based active is used as an active in the antiperspirant.

8. The process of claim 7, further comprising:

leaching the powder with water to create a solution;

filtering the solution to remove any undissolved particles; and evaporating the water from the solution to obtain water-soluble particles of the powder.

9. The process of claim 7, further comprising:

selecting a second plant material from *Hydrastis* sp., the second plant material being chosen from aerial parts of *Hydrastis* sp.;

grinding the second plant material into pieces;

performing extraction on the second plant material through a fluid extraction process to create a plant extract; and combining the potent plant based active and the plant extract to create the antiperspirant preparation;

incubating the antiperspirant preparation at a temperature of 30-100° C. for a time period between 1 hour and 6 weeks; and using the antiperspirant preparation in the antiperspirant.

10. The process of claim 8, further comprising:

selecting a third plant material from either *Salvia* sp. or *Cupressus* sp. the third plant material being chosen from aerial parts of *Salvia* sp. or *Cupressus* sp.;

distilling the third plant material with steam to create an essential oil from the third plant material; and combining the potent plant based active and the essential oil to create the antiperspirant preparation;

incubating the antiperspirant preparation at a temperature of 30-100° C. for a time period between 1 hour and 6 weeks; and using the antiperspirant preparation in the antiperspirant.

\* \* \* \* \*